United States Patent
Barragan I Plana

(10) Patent No.: US 12,415,111 B2
(45) Date of Patent: Sep. 16, 2025

(54) GARMENT

(71) Applicant: Sergi Barragan I Plana, Breda (ES)

(72) Inventor: Sergi Barragan I Plana, Breda (ES)

(*) Notice: Subject to any disclaimer, the term of this patent is extended or adjusted under 35 U.S.C. 154(b) by 0 days.

(21) Appl. No.: 18/720,040

(22) PCT Filed: Jan. 7, 2023

(86) PCT No.: PCT/ES2023/070004
§ 371 (c)(1),
(2) Date: Jun. 14, 2024

(87) PCT Pub. No.: WO2023/131734
PCT Pub. Date: Jul. 13, 2023

(65) Prior Publication Data
US 2024/0416170 A1    Dec. 19, 2024

(30) Foreign Application Priority Data
Jan. 8, 2022  (ES) .............................. ES202230025U

(51) Int. Cl.
*A63B 21/00*  (2006.01)
*A63B 21/06*  (2006.01)

(52) U.S. Cl.
CPC ...... *A63B 21/4025* (2015.10); *A63B 21/0602* (2013.01)

(58) Field of Classification Search
CPC . A63B 21/0602; A63B 21/4025; A63B 23/02; A41D 13/0015; A61F 5/0104; A61F 5/02
See application file for complete search history.

(56) References Cited

U.S. PATENT DOCUMENTS

| | | | | |
|---|---|---|---|---|
| 4,344,620 A | * | 8/1982 | Debski | A63B 21/065 2/102 |
| 4,951,940 A | * | 8/1990 | Vitello | B29C 43/003 224/148.1 |

(Continued)

FOREIGN PATENT DOCUMENTS

| | | |
|---|---|---|
| GB | 245037 A | 10/1925 |
| GB | 2352611 A | 2/2001 |
| WO | 9822052 A1 | 5/1998 |

OTHER PUBLICATIONS

International Search Report and Written Opinion, PCT/ES2023/070004, mailed Apr. 3, 2023.

*Primary Examiner* — Joshua Lee
(74) *Attorney, Agent, or Firm* — Master Key IP, LLP; Justin G. Sanders

(57) ABSTRACT

Different aspects of the invention relate to a garment comprising ballasts configurable in such a way as to strengthen the musculature of a particular area of the body, while at the same time allowing to carry out another activity, whether fun or therapeutic. In one aspect of the invention, the ballasts are arranged differently to treat different ailments. Different ballast arrangements comprise different configurations of mass applied per zone, the ballast arrangement on the surface of the body, and the pattern this ballast arrangement follows. Each arrangement generates different imbalances, and of different intensity, on the body, which, when carrying out other activities, has the combined effect of treating an ailment according to physiotherapeutic indications. The particular ballast configuration could be already defined on the garment, or can be configured and reconfigured by the user himself, following indications.

20 Claims, 11 Drawing Sheets

(56) References Cited

U.S. PATENT DOCUMENTS

| | | | | |
|---|---|---|---|---|
| 5,048,125 | A * | 9/1991 | Libertini | A63B 21/4007 2/79 |
| 6,485,446 | B1 * | 11/2002 | Brother | A61F 5/30 602/5 |
| 7,025,709 | B2 * | 4/2006 | Riggall | A63B 21/00189 2/160 |
| 7,650,648 | B2 * | 1/2010 | Roberts | A42B 1/08 2/200.1 |
| 8,156,572 | B2 * | 4/2012 | Whaley | A63B 21/4005 2/69 |
| 8,944,974 | B2 * | 2/2015 | Foster | A63B 21/00065 482/69 |
| 9,271,537 | B2 * | 3/2016 | Nelson | A42B 3/121 |
| 9,301,554 | B2 * | 4/2016 | Whaley | A41D 1/00 |
| 10,271,591 | B2 * | 4/2019 | Bangera | A63B 71/081 |
| 10,625,110 | B2 * | 4/2020 | Henneberry | A63B 21/06 |
| 10,645,980 | B2 * | 5/2020 | Rao | A63B 21/00 |
| 11,071,884 | B2 * | 7/2021 | Brummond | A63B 41/02 |
| 2003/0139258 | A1 * | 7/2003 | Riggall | A63B 23/03508 482/44 |
| 2007/0173385 | A1 * | 7/2007 | Cohenca | A63B 21/0602 482/105 |
| 2012/0102633 | A1 * | 5/2012 | Aulenbach | A41D 13/0575 2/455 |
| 2013/0298302 | A1 * | 11/2013 | Whaley | A63B 21/065 2/69 |
| 2014/0302970 | A1 * | 10/2014 | Sinclair | A63B 21/065 482/105 |
| 2015/0196790 | A1 * | 7/2015 | Escueta | A63B 21/0603 482/110 |
| 2016/0183605 | A1 * | 6/2016 | Leschinsky | A61L 2/18 2/247 |
| 2018/0027894 | A1 * | 2/2018 | Bangera | A41D 31/285 |
| 2018/0161616 | A1 * | 6/2018 | Henneberry | A63B 21/065 |
| 2020/0376324 | A1 * | 12/2020 | von Hoffmann | A63B 21/0004 |
| 2021/0360992 | A1 * | 11/2021 | Hamburger | A41D 13/015 |

* cited by examiner

FIG. 2
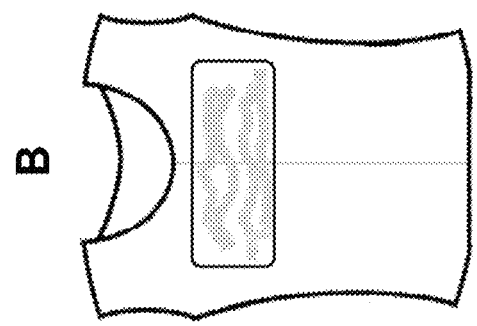
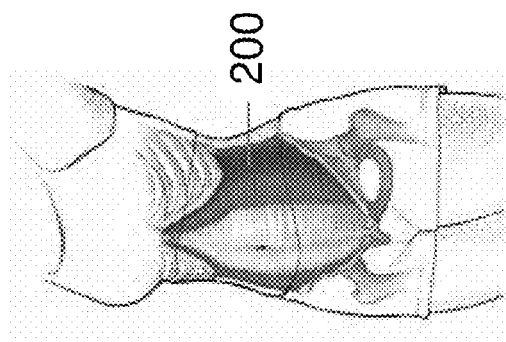
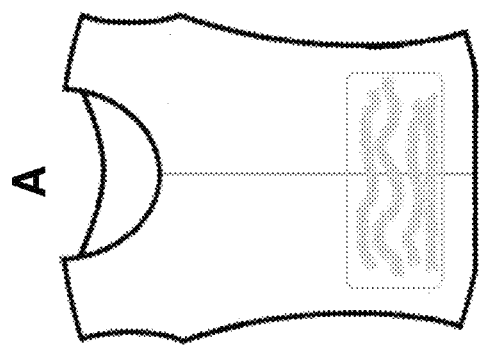

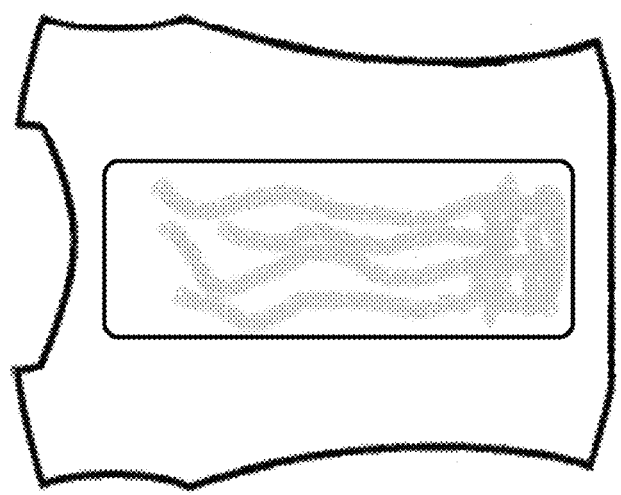
FIG. 4
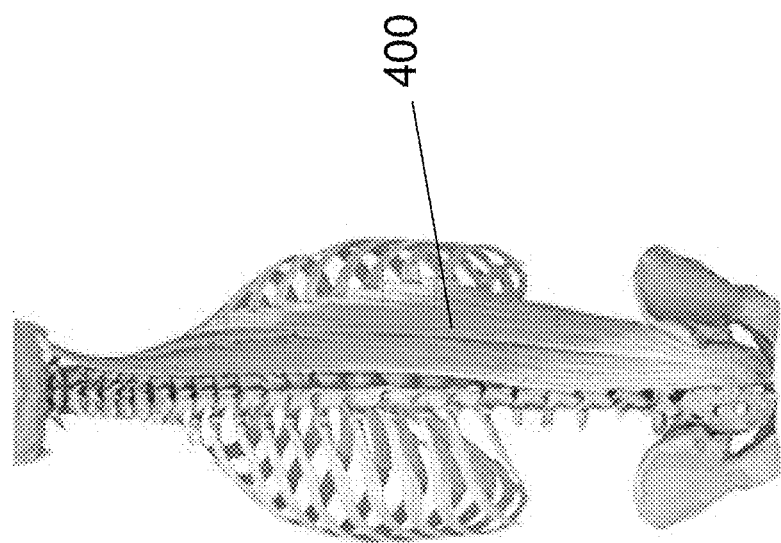
400

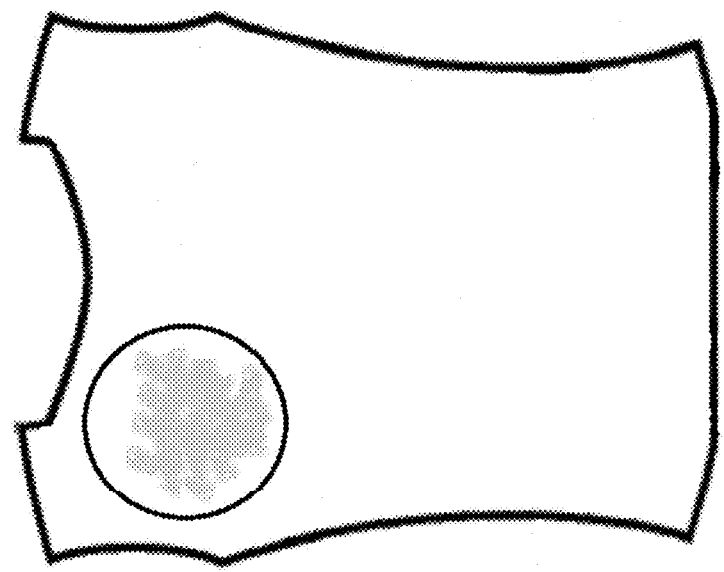
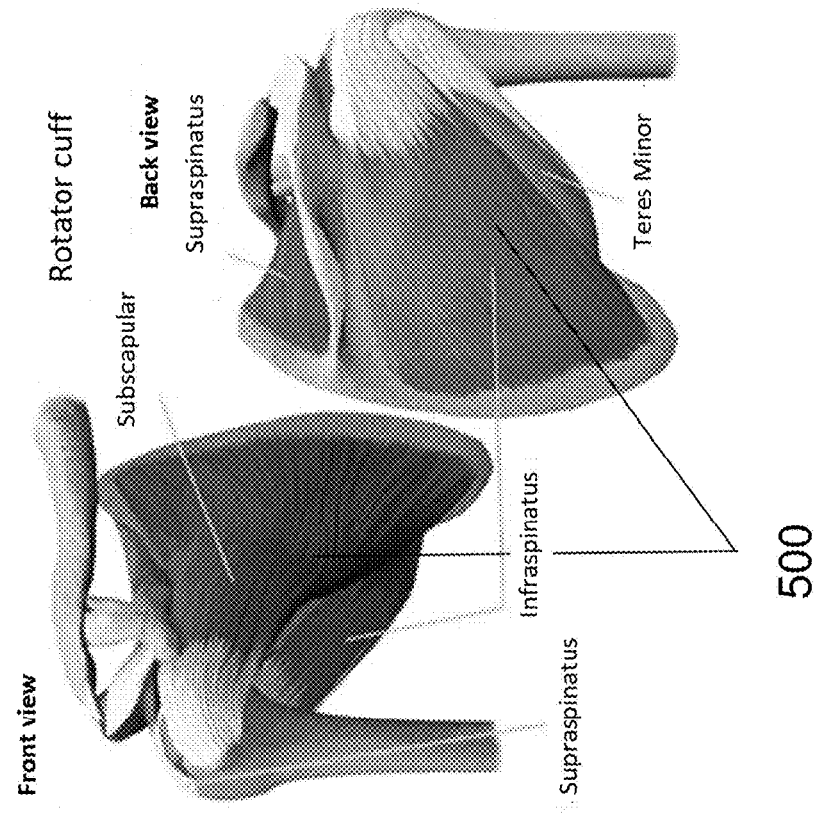
FIG. 5

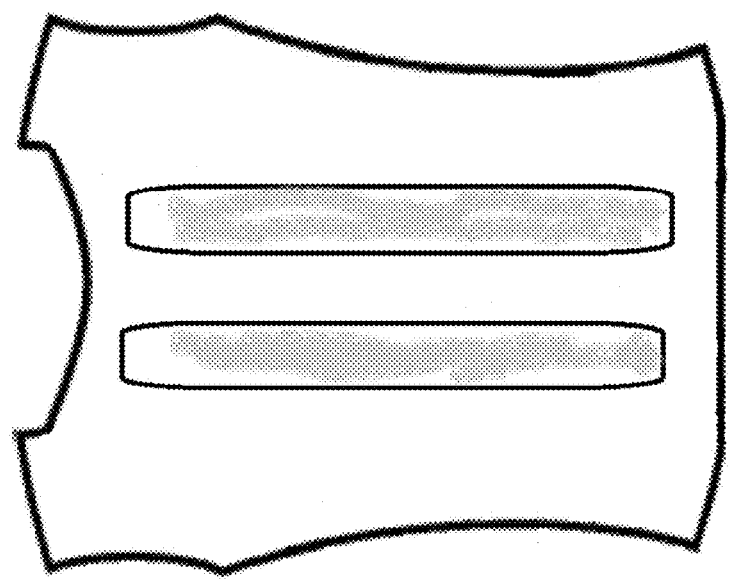
FIG. 6
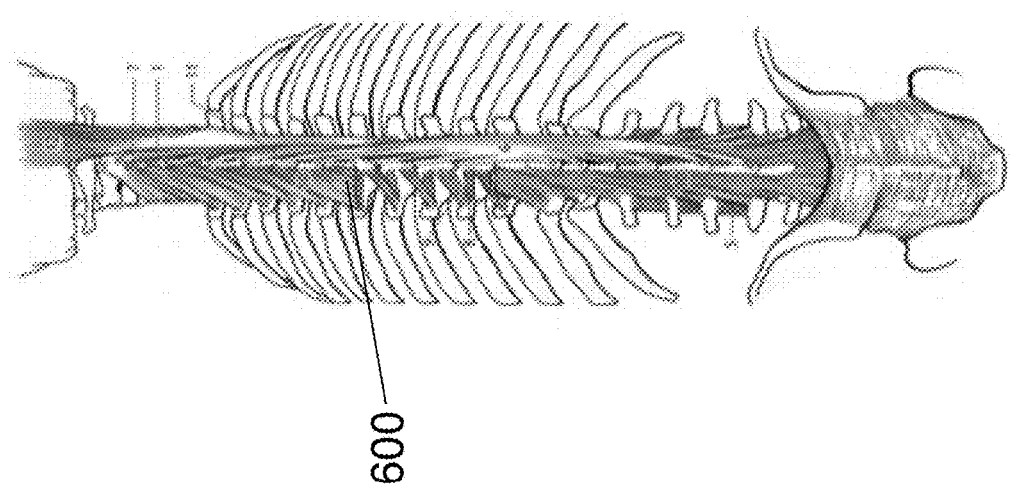
600

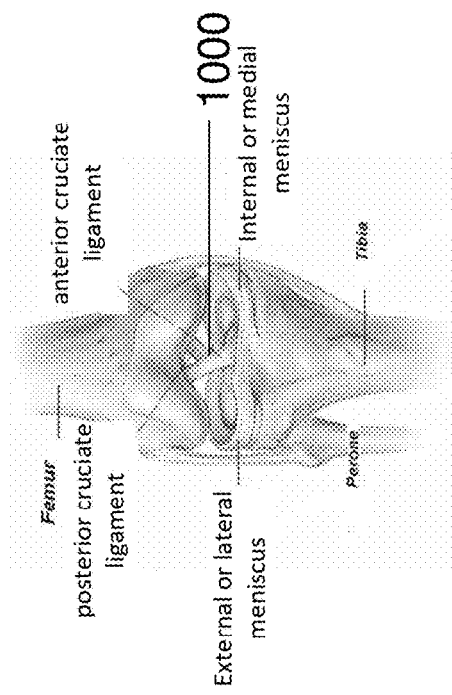
FIG. 10
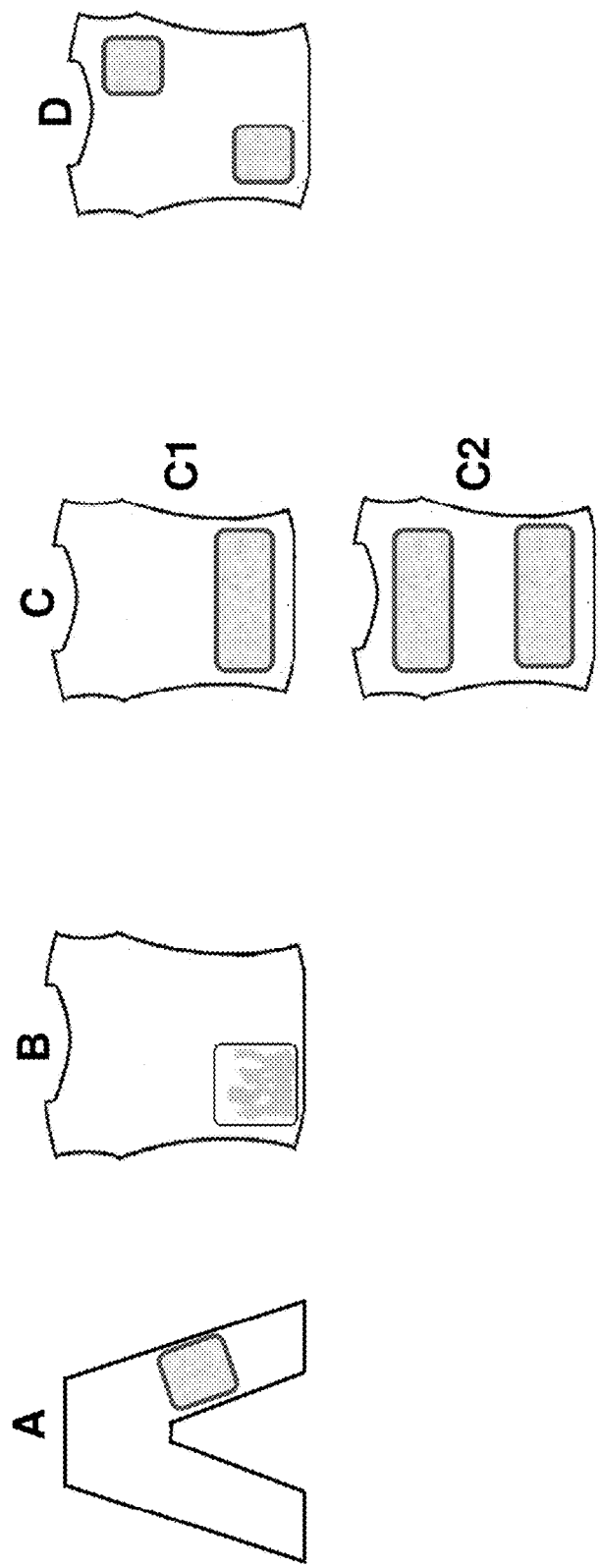

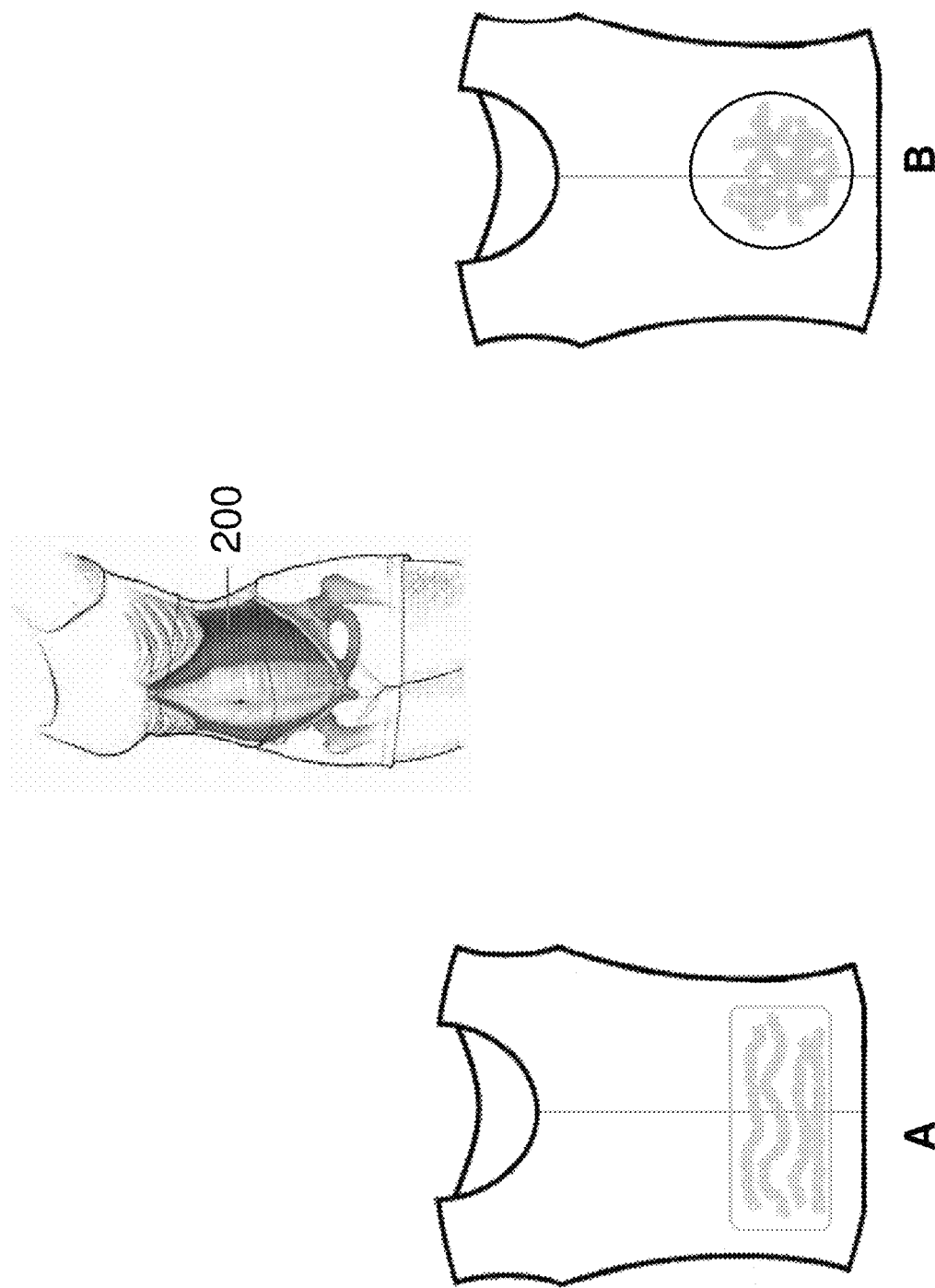

GARMENT

RELATED APPLICATIONS

This application is a 35 U.S.C. § 371 US national stage entry of International Application number PCT/ES2023/070004, filed Jan. 7, 2023, and claims priority and is entitled to the filing date of ES application number U202230025, filed on Jan. 8, 2022. The contents of the aforementioned applications are incorporated by reference herein.

FIELD OF THE INVENTION

The invention generally refers to the field of clothing, and in particular, deals with a garment that enables improving balance, stability and performance, both in daily life and in strengthening, rehabilitation, readaptation and other types of exercises.

BACKGROUND ART

The sedentary lifestyle, often due to work in front of the computer, that does not allow continuous movement of the body, is resulting in many injuries of various kinds, mainly in the back, but that can extend to the shoulders, neck, arms and legs alike. On the one hand, little physical activity, poor diet, bad lifestyle habits, or on the other hand, excessive exercise or very intense exercise in a short time, end up causing injuries such as:

At back and trunk level:
  Herniation and protruded disc.
  Sprains.
  Tendinitis.
  Surgical interventions of the spine.
  Postoperative.
  Spinal cord injuries.
  Scoliosis.
  Trauma (due to falls, work accidents, traffic accidents, and the like).
  Vertebral fractures.
  Rib fractures.
  Muscle weakness (bedridden, immobilized patients . . . ).
  Pathologies exhibiting deficit in balance: Parkinson's, stroke, ALS, Multiple Sclerosis, neurodegenerative diseases, and others.
  Respiratory pathologies (COPD, asthma, and so on).
  Low back pain.
  Cervicalgia.
  Dorsalgia.
  Adaptive body posture (incorrect and ineffective).
  Abdominal muscle weakness: postpartum, post-cesarean section, abdominal postoperative, aesthetic interventions (liposuction, abdominoplasty, and others).

Pelvis and Lower Extremities, EEII
  Pelvis fractures.
  Prolapse (bladder, uterus, and the like).
  Male and female urinary incontinence.
  Pelvic pain.
  Sexual dysfunctions.
  Postpartum.
  Lower Extremity Fractures, EEII, or Osseous Extremities Fractures, EESS.
  Tendinitis.
  Sprains.
  Neurological lesions (peripheral nerves).
  Knee prosthesis.
  Hip prosthesis.

Osseous Extremities, EESS
  EESS Fractures.
  Tendinitis.
  Sprains; of knee, hip, ankle, and others.
  Luxations.
  Neurological lesions (peripheral nerves).

Skull/face/neck
  Headaches.
  Migraine headaches.
  Dizziness.
  Vertigo.
  Neuralgia (trigeminal).
  Temporomandibular joint dysfunctions, ATM.

In the following, reference is made to two types of muscle with complementary functions; the unconscious musculature and the conscious musculature. The body constantly seeks to provide stability so that any other movement can be performed afterwards. Stability is generated by the unconscious musculature as a basis on which the conscious musculature produces body movements. In other words, in order to be able to perform any type of conscious movement, we need the unconscious musculature to stabilize the rest of the body. By way of metaphor, just as a crane needs to be anchored to the ground or to increase its support base with additional anchors in order to lift and move a great weight from one side to the other, the body needs to stabilize the base of the mobile areas in order to be able to perform any type of movement.

Currently, in the world of rehabilitation, readaptation and personal training, we work following the guideline that if the CORE (understanding CORE as all the muscles of unconscious activation that stabilizes the trunk and joints, thus facilitating the action of the conscious muscles that allows the movement itself) is active/strong, the rest of the body works more effectively and efficiently. This ends up improving the entire biomechanical functioning of the body, leading to better posture, helping to shorten recovery time from the injuries discussed above and minimizing the recurrence of injuries. On the other hand, in a healthy person, it improves their physical condition, prevents the appearance of such injuries and improves the overall health of the person.

In order to strengthen the muscles of the trunk and limbs, we have gradually moved from working with weights, in appropriate machines, to a more natural work. In this effort, the body's own weight and minimalist material are used to achieve more natural results that are more in line with the biomechanics and natural functioning of the body. We are not looking for a "swollen" body with a lot of power, but a "fit and healthy" body, able to withstand the day to day, as well as to perform more extreme activities in our free time: running several times a week, marathons, ultras, weekly paddle tennis matches, and so on.

There are many tools to work both strength and CORE at proprioception level (rubber bands, bosu, and others) but all these tools require a dedication focused on exercise, and do not allow freedom of movement to be able to devote, at the same time, to other activities. That is to say, there are no tools that allow working the CORE while doing other activities. The existing equipment to date is conditioned to create imbalances from an unstable floor (bosu), tractions with lateral and/or frontal rubber bands.

Other systems that work in this sense are also known, such as unstable bars or plates. Depending on the mass applied, they require more or less force and work on central stability. All these systems require the use of limbs to generate leverage and control the weights. Therefore, these alternatives suffer from the same problem of lack of freedom of operation and absolute dedication, not allowing to carry out other activities at the same time.

The applicant is not aware of any device that allows solving these problems as simply as the invention. Therefore, there is a need to effectively solve these described problems.

SUMMARY

It is an object of the invention to provide solutions to the above-mentioned problems, as defined by the independent claims. Preferred embodiments are defined by the dependent claims. In particular, it is an object of the invention to provide a garment comprising ballasts configurable in such a way that, according to their positioning and filling (more or less viscous), they allow to strengthen the musculature of a particular area of the body or several at the same time, while allowing at the same time to carry out another activity.

For example, a person suffering from low back pain, could wear the garment configured for this ailment, while simultaneously engaging in his or her favorite sport, for example, running. In this way, while running, the ballast configuration of the garment acts positively on the body, reducing the low back injury over time.

In one aspect of the invention, the ballast are arranged differently to treat different ailments. Each arrangement generates different imbalances, and of different intensity, on the body, which, when carrying out other activities, has the combined effect of treating an ailment according to physiotherapeutic indications.

In another aspect of the invention, it is not necessary to have an ailment to use the garment. Its mere use helps to strengthen the desired musculature, resulting in a healthier body that is less likely to suffer from pathologies. In this aspect, a particular configuration of ballast can also be used to obtain a desired body shape, such as the "fit and healthy" body mentioned above.

In all aspects, the particular ballast configuration may be already defined in the garment, or can be configured and reconfigured by the user himself, following indications.

BRIEF DESCRIPTION OF THE DRAWING(S)

The features and advantages of the present invention will become more apparent from the detailed description which follows in conjunction with the drawings, wherein like reference characters identify corresponding elements in different drawings. Corresponding elements may also be referenced by different characters.

FIG. 2 shows an example of application to the transverse abdominals.

FIG. 4 shows an example of application to the erector column.

FIG. 5 shows an example of application to the shoulder stabilizers.

FIG. 6 shows an example of application to the multifidus.

FIG. 10 shows an example of application to the anterior cruciate ligament ACL of the knee.

FIG. 11 shows two examples of application to the transverse abdominals with different directional effects.

DETAILED DESCRIPTION OF THE INVENTION

Figure 1:
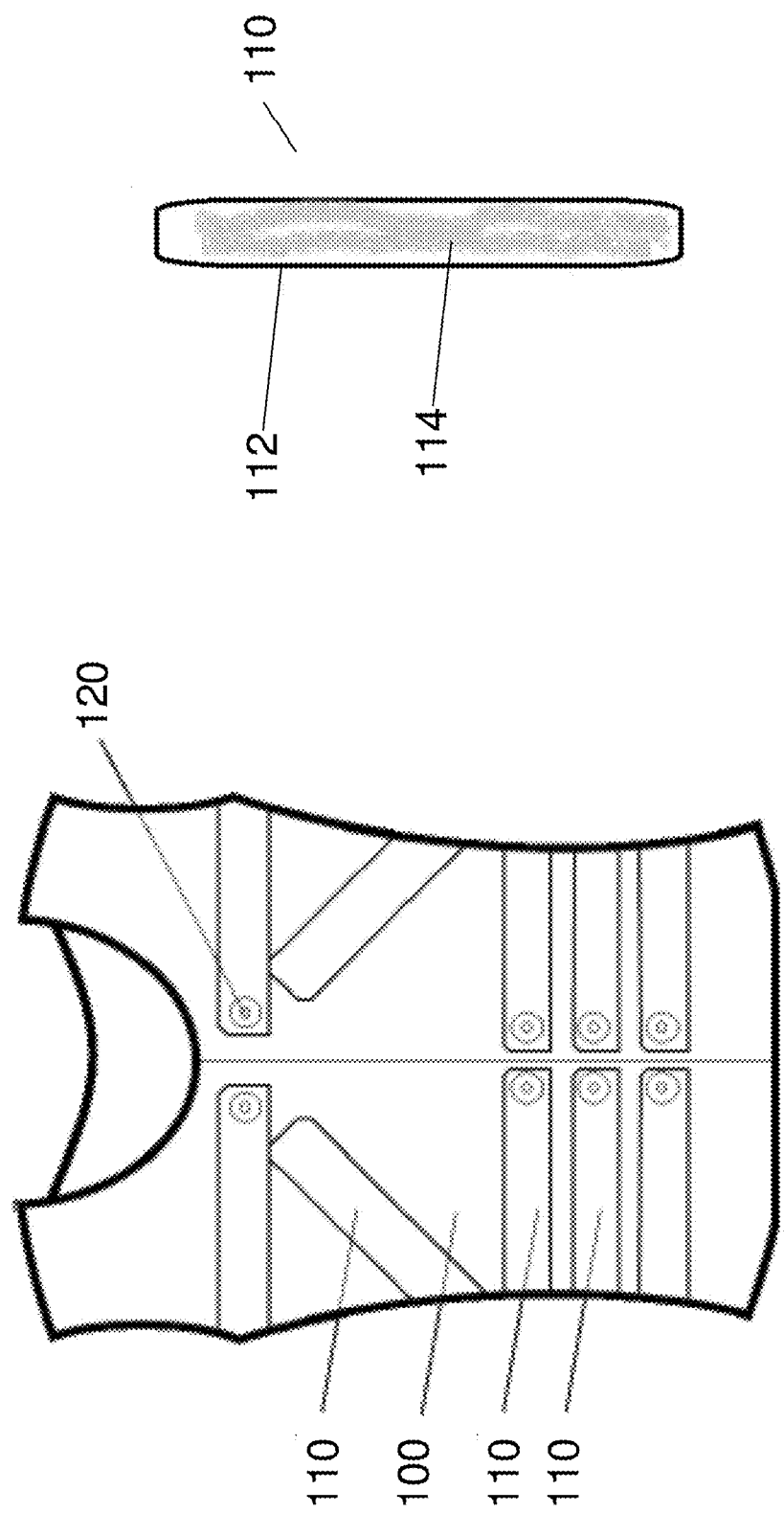
FIG. 1 shows a schematic front view of the garment in the form of a vest.

FIG. 1 shows a schematic front (anterior) view of a garment configuration 100. In this case, the garment is worn in the trunk area, as it is in the form of a vest. In this aspect, the garment comprises a series of fluid reservoirs 110, some of which are completely filled and some of which are held at less than maximum capacity to allow for further fluid displacement. The reservoirs are refillable, as enables by a plug 120. In this way it is possible to change their mass. As the reservoirs are filled with fluid, and thus the fluid is displaced with body movement, the movements of the wearer produce displacements of the masses of the garment. This produces forces in different directions and of different intensity that have to be counteracted by the user's musculature, achieving two objectives. The first and primary objective is to work on the stabilizing musculature (CORE), which, as we have already mentioned, is unconsciously activated and allows the stabilization of the worked area so that the second objective, the strengthening of the active muscles, can be achieved.

In the case of an upper garment, such as a vest, it will mainly be the trunk that is activated, although depending on the arrangement of the ballasts and the activity performed by the user, it will also work on the lower extremities (especially knees and ankles). The garment is designed to be worn while performing any type of activity, adding a constant CORE workout. Therefore, it provides muscular and physical improvements, improves posture and reduces the risk of future injuries. In addition, proprioception work stimulates the creation of receptors that send information to the brain and promote a faster and better reaction to any external force or alteration that may occur: unstable ground, tripping, stumbling, and others, thereby reducing falls and injuries. By having the ballast so close to the body, the risk of injury is reduced compared to other techniques.

The reservoirs may be detachably fixed to the garment. For example, they may have adhesive textile on one side while the garment has the other part of the adhesive textile. Likewise, they may have straps for attachment to hoops, hooks or the like on the garment. Likewise, they can also be incorporated inside the garment itself (in pockets already marking the direction of the same). The tanks are preferably of flexible walls, to seek a good adaptation to the different regions of the body, better comfort for the user, but also to increase the forces of action of the ballast.

As can be seen in FIG. 1, each ballast comprises a housing, or reservoir 112, for housing a filler 114 of viscous material, and the filler itself. The viscosity of the material allows the material to flow and move following the inertia of the user's own motion. Unlike solid ballasts, these viscous ballasts have an additional dynamic effect, helping the muscles involved to work harder with the same physical activity or exercise.

It is important that the filler is a viscous material, such as a liquid, since it exhibits the attributes of a fluid. One of the attributes is that, upon receiving energy through motion from the reservoir, the energy travels through the viscous filler by waves that have a certain inertia. The first wave may be more intense, but it is followed by subsequent waves, generated by the inner walls of the reservoir and of lower intensity. Thus, the dynamic effect is continuous over time and does not end abruptly. This effect is healthier for the body, especially the one under therapeutic treatment, as the muscles absorb and work on the same energy received, but in a less shocking way for the muscles, tendons and joints. Thus, viscous padding is healthier than solid padding.

Another of the properties of fluids is that it allows the generation of waves in various directions or axes. Thus, it is not limited simply to the direction of motion of the body, as would be the case with a solid fill. Even if the body moves in a unique direction, if the reservoir is sufficiently wide, it will allow the generation of waves in several directions, acting on the musculature in several axes.

This additional dynamic effect of the viscous filler has at least two components. The first "directional" effect seeks substantial displacement of the filler as the user performs the activity. For example, the ballasts of FIG. 6 are partially filled and arranged such that, as the user moves, the inner filling moves along the longitudinal axis of the ballast. As the torso reaches the end of a repetitive stroke (for example, when doing sit-ups, or rowing) the inertia of the padding causes its mass to continue to operate in the same direction of the original movement. Thus, for a period of time, the filler acts in the opposite direction to the reservoir that is attached to the user's body (which is already in the return path), and the muscles involved work harder to counteract this inertia of the filler. When the filler finishes its own path within the reservoir, a new return phase begins in the opposite direction, this time the direction of the reservoir and its filler being aligned. This cycle is repeated with each repetition of the exercise.

The shape, size and directional arrangement of the reservoirs can cause different directional effects. In one aspect, a purely "unidirectional" effect can be configured to work particular muscles, for example, as depicted in FIG. 6. In this aspect, the ballasts are elongated and arranged in the same direction as the tissues of the muscle on which they act (that is, the longitudinal axis of the ballast is parallel to the main axis of the muscle). This ensures that the filler is substantially displaced within the reservoir, focusing its directional effect precisely on the muscles, in this case, the multifidus.

In another aspect, an "omnidirectional" effect can be configured to work the muscle in a general way, for example, as depicted in FIG. 5. In this aspect, the aim is to act on the shoulder stabilizers in various directions. Accordingly, a ballast is configured in a rounded shape arranged over the muscle on which it acts. In conjunction with the type of exercise carried out, this ensures that the filler moves in all directions within the tank, focusing its directional effect in all directions on the desired muscle. In yet another aspect, if the ballast is disposed elsewhere in the body, this omnidirectional displacement is achieved by acting on several muscles, causing a plurality of muscles to be strengthened as the exercise is carried out.

FIG. 11 depicts an example wherein one can act with different directional effects on the transversus abdominals of FIG. 2. Scheme A on the left, representing the front (anterior) view of the vest, depicts the ballast with unidirectional shape, size and arrangement to primarily strengthen the transversus abdominis (for example, by rotating the torso in both directions, or by doing sit-ups). Scheme B on the right, represents the ballast with shape, size and omnidirectional arrangement to strengthen all the different muscles of the abdominal area (for example, running or jumping rope).

While the first "directional" effect seeks substantial displacement of the filler as the user performs the activity, in another aspect, a second "massive" effect seeks little displacement of the filler, but does require a great deal of effort as the user performs the activity. This is achieved by having a high viscosity, high density (or high mass) filler. Here the directional effect is reduced as the main effort of the muscles is focused on carrying out the movement given the high mass of the ballast. However, even if the reservoir is completely filled, the ballast still exhibits the same attributes of the effect of fluids.

The liquid will normally be water, but another liquid of different density can be used, for example, a gel of higher or lower viscosity. In activities with little movement and wherein it is important to better maintain the posture (yoga, pilates, and so on) increasing the density of the liquid using a more viscous material helps to slow down the velocity of the liquid inside the reservoir and allows the body's readaptation to the weight variation caused by the ballast to be slower and more constant. This can be particularly interesting for therapeutic applications. If we are looking for a more imbalanced and stabilization work in activities with higher movement, the ballast can be of identical characteristics, but less viscous, giving more prominence to the imbalance caused by the multiple directions in which the liquid will move when performing the exercise (forcing the CORE to thousands of micro adaptations made by the unconscious musculature in order to stabilize the body in each of the directions in which the filling moves). On the other hand, if in these same activities we are looking for more strength work, the reservoirs are filled with denser fluid, giving more prominence to the weight than to the direction, thus achieving a greater work of the conscious musculature.

The density of the viscous filler is therefore configurable. In one aspect, a higher density filler makes it possible to better accompany slow movements in search of a workout of the unconscious musculature (CORE) and this same filler also allows a more forceful workout in activities with greater dynamism (on conscious musculature). In another aspect, a higher density filler also allows a more comfortable feeling when doing very dynamic or even abrupt movements, such as jumping. In yet another aspect, a less viscous filler (lower density, like water) allows for a better accompaniment of less abrupt movements and where you want to work more intensely the muscles involved (conscious), for example, multiple repetitions of leg or arm lifts, or torso movements. Similarly, with more abrupt and dynamic activities, continuing with the example of jumping, more liquid and lower density ballasts allow a more focused work on the CORE due to the multi-directionality that the liquid will have inside the tank. Thus, viscosity is configured differently depending on the purpose of the activity. In recreational activities, it can be configured according to the user's taste, who depending on the activity in question (running, rowing, swimming), can take advantage of the additional strengthening provided by the ballast garment, but at the same time feel more comfortable with the sensation of wearing it. In therapeutic activities, it can be configured following indications of physiotherapists to improve the pathology being treated.

Preferably the reservoirs are refillable, either to modify the mass or to store the garment without the liquid. Furthermore, it is preferable that the reservoirs are removable for readjusting them, storing them separately, increasing or decreasing their number. In addition, when they are fillers, handling is facilitated if they are removable. However, it has been frequently found that when filling the ballast partially, the housing collapses in the area where there is no viscous material, making it difficult to move the viscous material along the entire length and width of the ballast. This prevents the desired effects from being obtained. Therefore, in one aspect the ballast is configured to allow both liquid and air to be introduced. The air fills the housing completely in the areas where there is no viscous material, thus achieving unimpeded, easier and multi-directional displacement of the viscous material.

While, in one aspect, the reservoir is partially filled with the viscous material, allowing room for displacement, in another aspect the reservoir is completely filled with viscous material. This is because, depending on the viscosity of the filler (especially the lower the viscosity), even if there is no space for displacement, by exhibiting the attributes of a fluid, the filler will generate the aforementioned dynamic effect anyway, by transmitting energy through the fluid medium in different directions. However, in yet another aspect, a reservoir can also be configured with a reservoir exhibiting a certain elasticity. That is, by having elastic walls, even if the reservoir is completely filled with viscous material, an additional stronger dynamic effect will be generated than with solid, inflexible walls.

In another aspect, a plurality of non-fillable ballasts may be disposed, but of different sizes and shapes. The non-fillable ballasts are airtight, having a particular viscous material and air distribution, allowing the desired viscous material to flow. As they are available in different sizes (large, small), different numbers of ballasts can be arranged to vary the applied mass. Also, as they are available in different shapes (elongated, wide, narrow, round), they can be better adapted to the shape of the body that will wear the garment. The dimensions and shapes of the tanks vary according to the activity, work area and above all according to the type of work we are looking for and the objective and condition of the user. In general, the reservoirs will be elongated and can store from 10 ml to 4000 ml of liquid.

The garment wherein the tanks are anchored, hooked, or placed will vary according to the area to be worked, the objective of the work and even the activity to be performed by the user. We find vest-type garments for the trunk, gloves for the hands and fingers, shoes/shoes for ankle and foot work, pants for specific hip, knee and ankle work, long sleeve blouses for shoulder, elbow, back work, and so on. In the same way, you can work with one or several garments and one or several ballasts depending on the objective and characteristics of the user. You can work from a preventive point of view, health improvement, injury treatment, even high-performance work. Always configuring the position, the number, the payload of the ballast, volume and the activity to be performed. Being able to work from a very general vision to something very concrete and specific.

The material of the garment is configured for the primary type of exercise. For example, a garment may be configured of a material that allows perspiration while the wearer runs, or another material for aquatic activities.

The reservoirs are preferably elongated, of different widths and may be in different directions. Thus, the displacements of the ballasts have different geometrical components. The reservoirs are elongated to define a main direction of movement. Each reservoir can have its own main direction, which will be different or parallel to each other. The position of the ballast looking for a specific direction of work allows us to affect different aspects within the same muscle and the same movement. In the case of looking for a more proprioceptive work, performed by the unconscious musculature (CORE), as the body constantly seeks to provide stability so that subsequently any other movement can be performed, we will use the ability to place the ballast in the direction of the muscle fibers that we intend to work to maximize the work of these stabilizers. By increasing the force vectors applied to the muscle fiber of the muscle to be worked, on the one hand, we force a greater work of force on the muscle itself. On the other hand, it forces a constant readjustment of the stabilizers (CORE) caused by the ballast(s) themselves. And, on the other hand, taking into account that for each action of a muscle (agonist) we have another muscle that works in the opposite way (antagonist), for example the biceps and triceps (when one contracts, the other must relax, otherwise the movement of the upper limb cannot be carried out), the placement of the ballast in the direction of the fibers of the agonist muscle allows a concentric work of this muscle at the same time as an eccentric work of its antagonist. When one flexes the arm, the other resists the flexion in a controlled manner so that the movement does not get out of control, preventing it from acting as a spring or impeding the movement. For this reason, the ballasts are configured in such a way that they are parallel to the direction of the muscle tissue on which they act. Multiple ballast can be placed in multiple directions (each following the direction of the muscle to be worked) for simultaneous work of different muscles. In the case of looking for a more focused work on strength, in addition to playing with the payload and viscosity of the ballast, we will increase the number of weights. In this case, several of them can be placed, alternating the direction so that at least one of them is placed in the direction of the fibers to be worked, but the rest can be placed perpendicular to the fibers and even away from the muscle to be worked, but in the direction of the movement to be performed. In this way it is possible to increase the payload by playing with the leverage provided by placing the ballast away from the musculature involved in the movement performed (for example, placing a ballast following the fibers of the quadriceps and another ballast in the ankle to work the quadriceps. The former works in the direction of the fibers enhancing proprioception, and with the latter on the ankle, the payload is increased and the action performed by the former is enhanced. By moving the ballast away from the work area, and placing it on the same axis as the muscle, the leverage is increased and therefore the work on the first ballast is increased. Another example can be seen in anterior cruciate ligament work, where we use the trunk garment with different ballast arrangements to enhance the work on the knee).

A user looking for rehabilitation will have to work with little ballast initially, increasing both in filler volume, number of reservoirs and combinations in the arrangement of the reservoirs. Even using different garments to follow a progression to reach a situation even better than the user had before the injury. The following describes examples of implementation applied to both strengthening and rehabilitation.

FIG. 2 shows an example of application to the transverse abdominal 200. The upper diagram shows the transverse abdominis, which in this case is the muscle to be strengthened or rehabilitated, and the lower diagram shows the corresponding ballast arrangement in two alternatives A (left) and B (right), both in front (anterior) view of the vest. In the example of arrangement A, the ballast is placed on top of the aforementioned muscle, so that the ballast is placed in the direction of the fibers, favoring a very analytical work, seeking action-reaction of the same muscle fibers, a stabilization work (when a displacement occurs in one direction, the fibers of the transverse act by resisting the movement as a counterweight and slowing down the inertia). In arrangement B, the ballast is placed above the muscle, away from it but located on the same axis of movement, thus acting on the same fibers but adding leverage work. This will increase the payload on these fibers while activating the antagonist and stabilizing muscles that complement it.

The transverse abdominal intervenes in:
Maintaining a correct posture.
Maintaining intra-abdominal pressure.
It is an expiratory muscle.
Participates in urination and defecation.
It is activated during labor contractions.
It has synergy with the pelvic floor.

The guidelines to follow to strengthen or rehabilitate could be (along the lines of what has been described above), for example:

Using arrangement A, perform some Kegel exercises (more positional exercises). In this case we would start with a single ballast in the position shown, getting the maximum work by filling it with a more viscous fluid, so that the displacement slows down slowly and progressively. With this we achieve a more intense activation of the muscle fibers themselves, favoring the work of the muscle itself well above the intensity required in normal exercise. Next, and to continue progressing within the same exercise, we can add to arrangement A, arrangement B (both at the same time), further increasing the work of the oblique muscles and creating a more global work by joining other muscle groups synergistic to this same muscle. Objective: enhanced urinary incontinence.

Perform plank exercises using arrangement A: we can differentiate between the "classic plank" and the lateral plank. The ballast arrangement will also be the same, but in the first case, classical plank, the progression goes through the arrangement of FIG. 4, thus increasing the payload on the lumbar area and forcing a much more intense work of the transverse. In the case of the lateral plank, we start with layout A but progress with FIG. 4 and we can even add FIGS. 8 and 9 (progressively). As described above, arrangement A and FIG. 4 comprise a thicker filler to achieve a slower and more harmonic displacement forcing the transversal abdominal to readjust its position slowly and steadily, but by adding FIGS. 8 and 9, we increase the leverage, as they are much more distal, and therefore the intensity of the work to be performed by the muscle. If in FIGS. 8 and 9 the fillers are configured of lower density, the effect is that the exercise is much more intense and the muscle is forced, on one hand to a slow and progressive stability control caused by the ballast of arrangement A and FIG. 4 (performed by a transverse abdominal in stabilizing function) and, on the other hand, to a much more dynamic and explosive work caused by the same muscle and its synergists (in much more dynamic function). Objective: prevents uterine or bladder prolapse and promotes postural control.

Performing breathing exercises using arrangement A: enhanced respiratory function.

Performing the same exercises but combining arrangements A and B in order to increase the work.

Performing hypopressive exercises using arrangement A: increases abdominal muscle tone after childbirth.

Performing trunk rotation exercises using arrangement A. Perform using arrangement A and B the same rotation exercises.

Running initially with arrangement A and progressing to arrangement B to end up combining A and B. The progression of the last three points is aimed at increasing muscle tone while improving proprioception. Thus achieving, among other things, enhanced posture, increased performance and muscle strength, creation of muscle and joint receptors.

Figure 3:
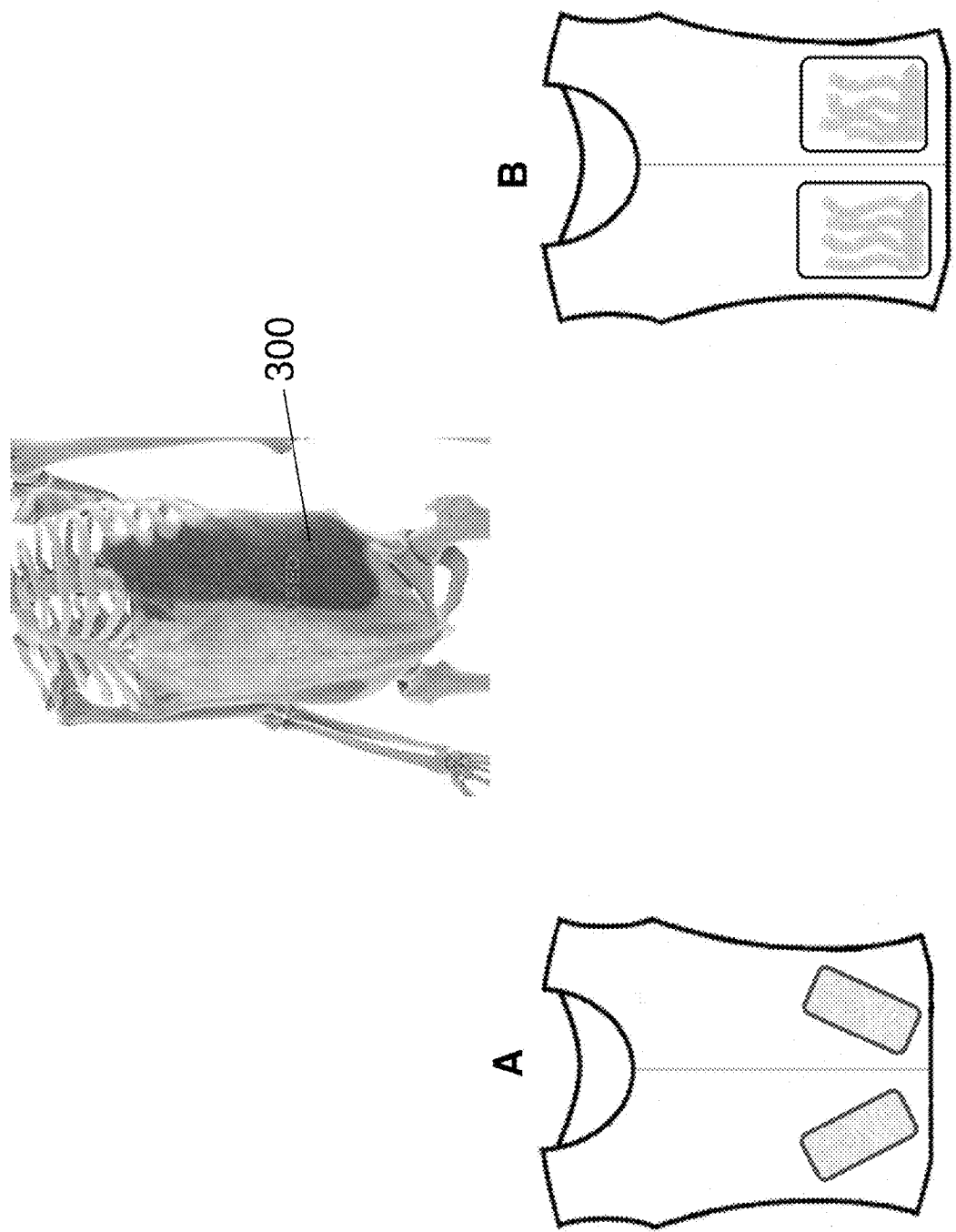
FIG. 3 shows an example of application to the obliques of the abdomen.

FIG. 3 shows an example application to the abdominal obliques 300. The upper diagram shows the abdominal obliques, which in this case is the muscle to be strengthened or rehabilitated, and the lower diagram shows the corresponding ballast arrangement in two alternatives A (left) and B (right), both in front (anterior) view of the vest.

The obliques of the abdomen are involved in:
Trunk flexion.
Rotation and inclination of the trunk.
Trunk stabilizers.

The guideline to follow to strengthen or rehabilitate could be, for example:

Performing ball kicking exercises using arrangement A: enhances proximal stability for greater efficiency at the distal level (lower extremity) and prevents possible injuries to the lower extremity and back. For example, for a soccer player.

Performing cardio class exercises using arrangement A: increase of muscular strength (rib fracture, abdominal surgery with loss of muscle mass . . . ).

Performing racket sport exercises using arrangement A: enhanced proximal stability for greater distal efficiency (tennis player, golfer).

Performing upper extremity proprioceptive exercises using arrangement A.

Performing hip stabilization exercises using arrangement B: increase the strength of the hip musculature and improve the stability of the coxofemoral joint after a hip prosthesis or femur fracture.

Performing balance exercises using arrangement B: enhanced balance and increased muscle strength on the affected side in hemiplegic patients.

FIG. 4 shows an example application to the erector spinae 400 comprising a complex group of muscles accompanied by tendons spanning the lumbar, thoracic and cervical area. It has fascicles that attach to the skull, cervical, thoracic and lumbar vertebrae (also at the sacrum and ilium). Its function is to maintain the spine erect. The diagram on the left shows the erector spinae, which in this case is the muscle to be strengthened or rehabilitated, and the diagram on the right shows the corresponding ballast arrangement in rear view (back) of the vest.

The guideline to follow to strengthen or rehabilitate could be, for example:

Performing a static plank: prevent or reduce symptoms of disc herniation, prevent or enhanced low back pain, improve posture . . . .

Practicing running: improving posture, strengthening the posterior musculature and preventing low back pain, dorsal and cervical pain, and similar.

Balance exercises: enhanced balance in bedridden people and/or elderly people (to prevent falls), improve proprioception in athletes to prevent injuries to both spine and EEII.

FIG. 5 shows an example application to the shoulder stabilizers 500 involved in glenohumeral stability for correct and effective movement of the entire upper extremity. The diagram on the left shows the shoulder stabilizers, which in this case is the muscle to be strengthened or rehabilitated, and the diagram on the right shows the corresponding ballast arrangement in rear (back) view of the vest.

The guideline to follow to strengthen or rehabilitate could be, for example:

In standing position, throwing a ball: enhanced proprioception of the shoulder after surgery or ligament injuries (tennis player, golfer, swimmer . . . ).

Bosu plank: enhanced proprioception and shoulder stability after dislocation, surgery, ligament injury, frozen shoulder, capsulitis, and so on.

Perform occupational therapy in patients with hemiplegia.

Perform daily routine activities: enhanced the entire joint and muscle complex of the shoulder after surgery, fracture, ligament injury, and so on.

FIG. 6 shows an example application to the multifidus 600, which provides stability in the spine. The diagram on the left shows the multifidus, which in this case is the muscle to be strengthened or rehabilitated, and the diagram on the right shows the corresponding ballast arrangement in rear (back) view of the vest.

The guideline to follow to strengthen or rehabilitate could be, for example:

Dynamic plank: strengthen the stabilizing muscles of the spine, correct posture, prevent herniated discs, improve the symptoms of osteoarthritis, prevent pain from prolongated postures, post-surgery of the spine.

Tai Chi practice: to strengthen the stabilizing muscles of the spine, correct posture, enhance balance and prevent falls in elderly people.

Perform an exercise program with dumbbells: to strengthen the stabilizing muscles of the spine, correct posture, enhance the symptoms of scoliosis and prevent its progression.

Figure 7:
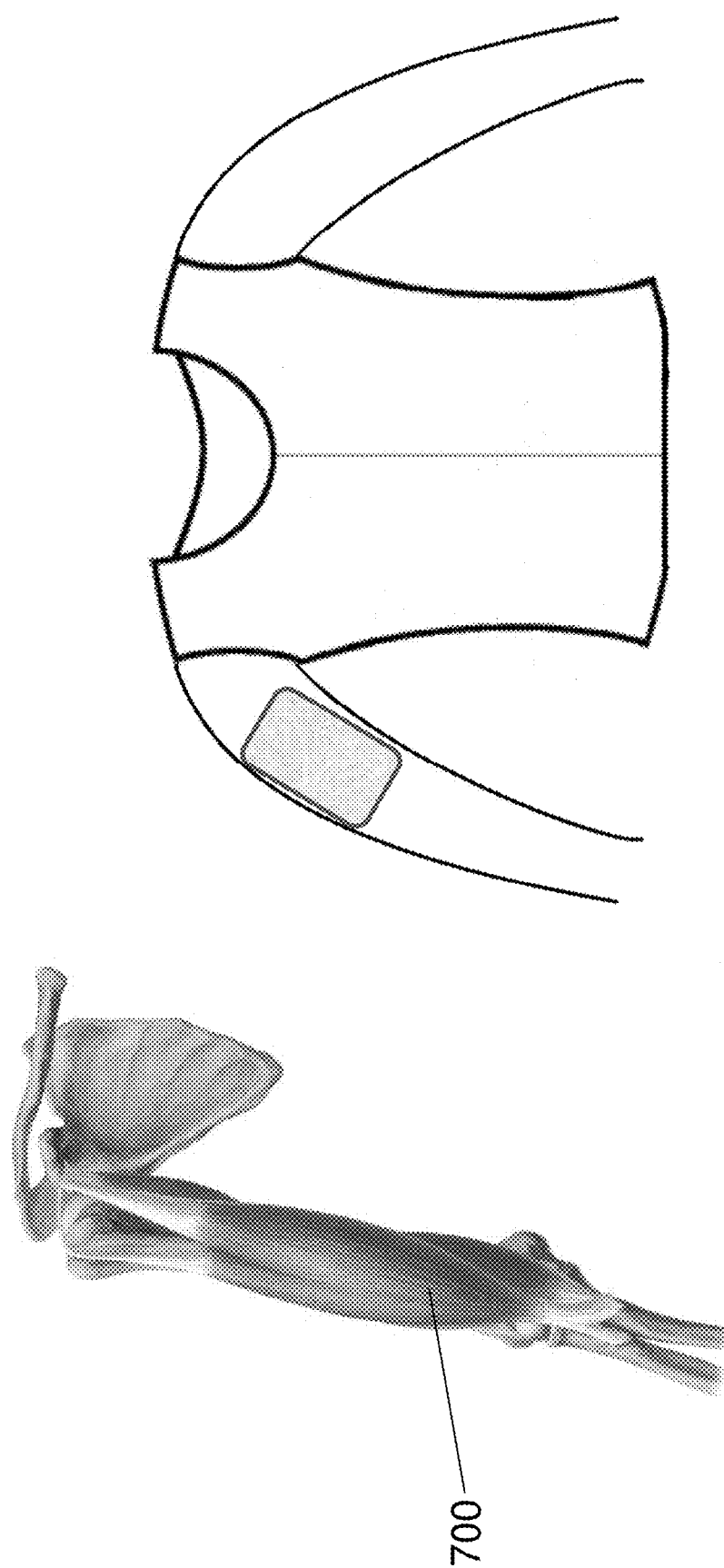
FIG. 7 shows an example of application to the brachii biceps.

FIG. 7 shows an example application to the biceps brachii 700, which performs flexion movement and supination of the elbow and participates in shoulder stabilization.

The diagram on the left shows the biceps, which in this case is the muscle to be strengthened or rehabilitated, and the diagram on the right shows the corresponding ballast arrangement in front (anterior) view of the vest.

The guideline to follow to strengthen or rehabilitate could be, for example:

Racket sports: increase biceps muscle strength after a partial rupture of the biceps tendon.

Proprioception exercises of the upper extremity: to restore the proprioceptive system at the shoulder and elbow after a shoulder luxation.

Exercises with elastic bands: to increase muscle balance after a humerus fracture.

Figure 8:
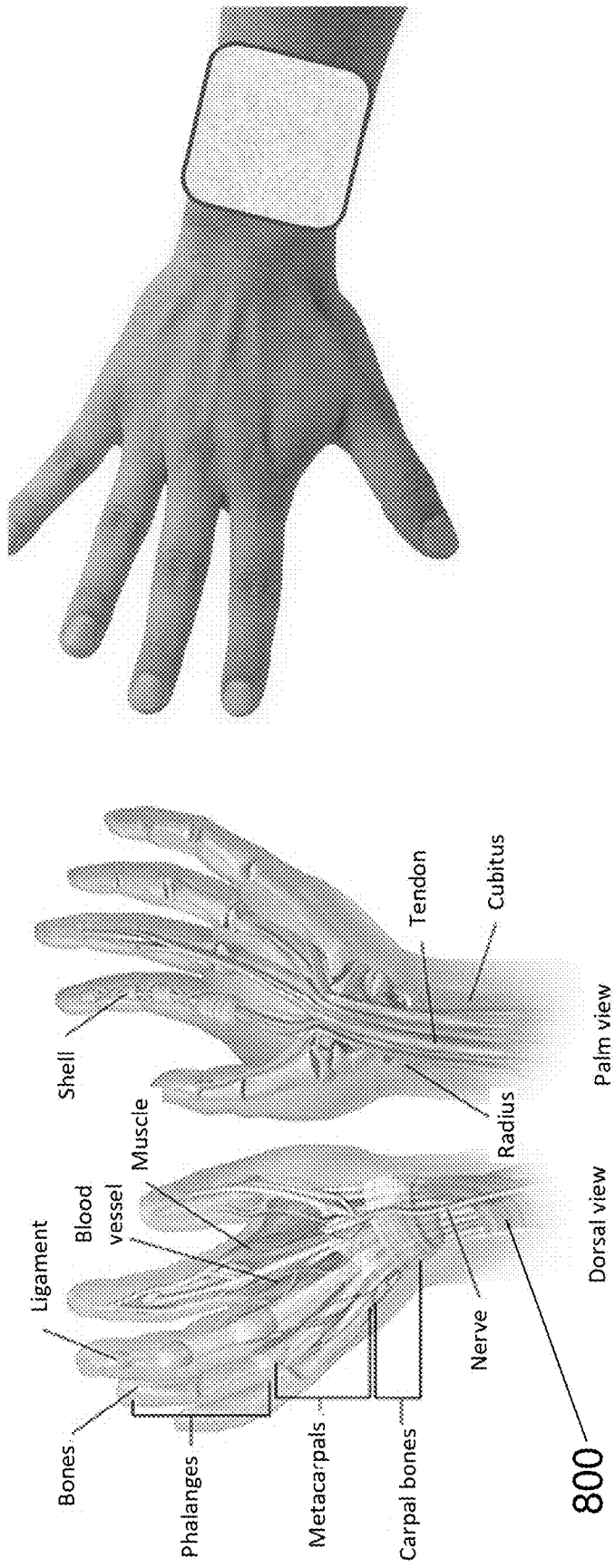
FIG. 8 shows an example of application to the wrists.

FIG. 8 shows an example application to wrists 800. The wrist connects the hand to the forearm. It is not a single large joint, but several small joints. This makes it flexible and allows your hand to move in different ways. The wrist has two large forearm bones and eight small bones called carpals. It also has tendons and ligaments, or connective tissues. Good stabilization of the wrist allows for proper movement of the hand and fingers, which is of great importance when performing manual activities such as typing. The diagram on the left shows the wrists, which in this case is the muscle to be strengthened or rehabilitated, and the diagram on the right shows the corresponding ballast arrangement in frontal (anterior) view.

The guideline to follow to strengthen or rehabilitate could be, for example:

Reaching for a ball: restoring quick grip after a peripheral nerve section.

Closed Kinetic Chain Exercises: enhance proprioception of the wrist complex and increase joint range after carpal tunnel surgery.

Figure 9:
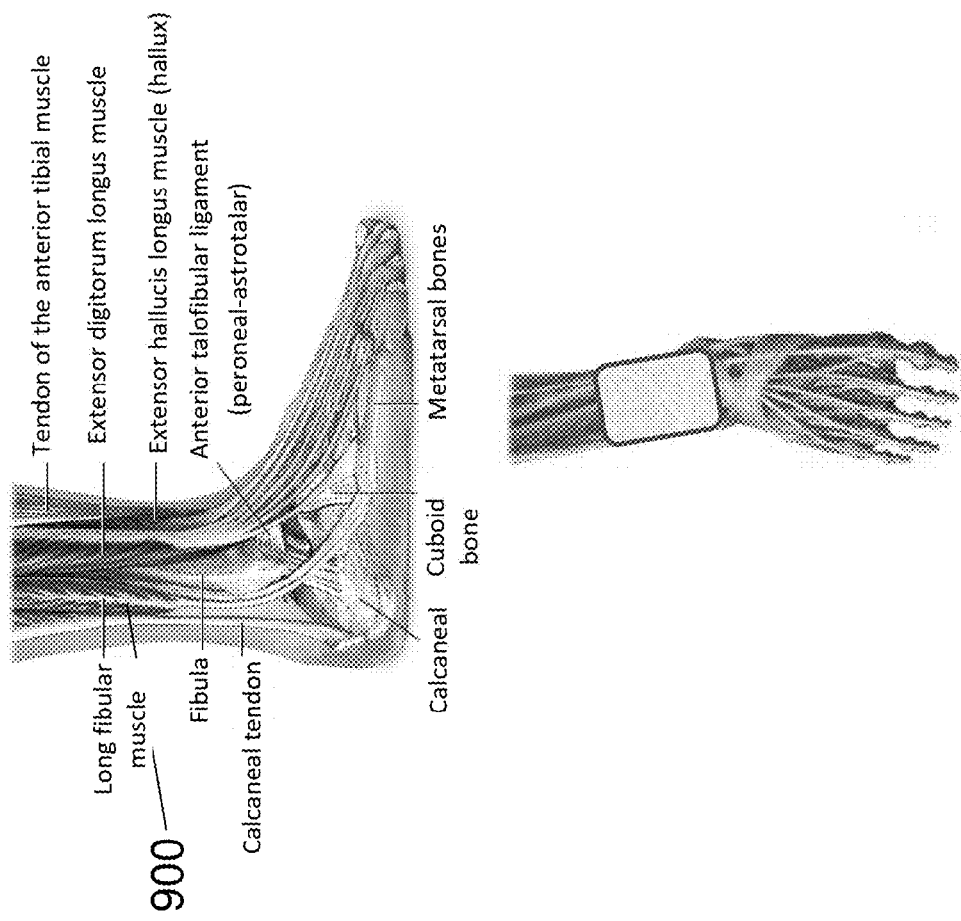
FIG. 9 shows an example of application to the ankles.

FIG. 9 shows an example application to the ankle 900. The ankle bone (talus) and the lower end of the two leg bones form the ankle joint. Ligaments, which connect the bones together, stabilize and support the joint. Muscles and tendons move it. The most common problems of the ankle are sprains and fractures. The upper diagram shows the ankle joint and the various tendons and muscles that comprise it, which in this case is the muscle to be strengthened or rehabilitated, and the lower diagram shows the corresponding ballast arrangement in front (anterior) view.

The guideline to follow to strengthen or rehabilitate could be, for example:

In a standing position and on one leg, holding the balance with eyes closed: enhanced ankle ligament proprioception after an ankle sprain.

Walking or running: increase joint and muscle range, improve proprioception after a fracture.

FIG. 10 shows an example application to the knee anterior cruciate ligament ACL 1000. The upper diagram shows the anterior cruciate ligament of the knee, which is desired to be strengthened or rehabilitated, and the lower diagrams show the corresponding ballast arrangements.

The fundamental role of the ACL is to provide stability to the knee, preventing excessive forward movement of the tibia. It is a limiter of knee hyperextension, limiting internal rotation of the knee, particularly when the knee is in extension. Anterior cruciate ligament injuries commonly occur during sports that involve sudden stopping or changing direction, jumping and landing, such as basketball, soccer, American football, and downhill skiing, for example:

Reduce speed and change direction suddenly (abruptly).

Turn around with the foot firmly supported.

Landing awkwardly after a jump.

Stopping suddenly.

Receiving a direct blow to the knee or collision, such as a tackle in an American football game.

The guideline to follow to strengthen or rehabilitate could be, for example:

In arrangement A, perform jumping exercises: regain muscle strength and restore the proprioceptive system after an ACL sprain.

In arrangement A, perform exercises involving change of direction and speed running: advanced phase of recovery after ACL surgery.

In arrangement A, perform squat exercises: increase muscle strength in the intermediate phase after ACL surgery.

Proper training and exercises can help reduce the risk of anterior cruciate ligament injury. A sports medicine physician or physical therapist can provide a good rehabilitation program for both prevention and recovery. Multiple studies show that a good functioning of the CORE, helps prevent and improve possible injuries, and contributes to a good functioning of the limbs, providing normal and efficient movements.

A progression in the rehabilitation of an anterior cruciate ligament of the knee is shown below. FIG. 10A shows, in front (anterior) view, a pant garment with a first ballast arrangement in the knee area. FIG. 10B shows, in rear (back) view, a vest garment with a second ballast arrangement in the lower left lumbar area. FIG. 10C1 shows, in rear (back) view, the vest garment with a third arrangement of ballast throughout the lower lumbar area. FIG. 10C2 shows, in rear (back) view, the vest garment with a fourth arrangement of ballast throughout the lower and upper lumbar area. FIG. 10D shows, in rear (back) view, the vest garment with a fifth arrangement of ballast in the left lower lumbar area and the right upper shoulder area, arranged diagonally opposite each other.

As the main injury is in the knee, we start with exercises that work directly the affected area and the trunk as secondary. In this case, to the exercises typical of this type of rehabilitation, we initially incorporate the trouser garment and the ballast weights in the front part of it, as in the first arrangement of FIG. 10A. The ballast weights are filled from less to more, following the evolution of the patient, the less liquid the less intensity of the exercise, the more liquid the greater the complexity and effort of the exercise. What is sought is to create greater instability in the knee joint.

The exercises to perform would be:

Set 1
 Objective: To gain CORE stability on the side opposite the affected side followed by proprioceptive and muscular work of the affected knee.
 Examples:
  Shooting the ball with the affected leg.
  Keeping a limp on the affected leg.
  Squats on the affected leg.
  Jumps on the affected leg.

Set 2
 Objective: analytical work of the lower abdominals. To increase muscle strength and enhanced reflex contraction.
 Examples:
  Static plank, dynamic plank, lateral plank.
  Bridges (pelvic retroversion).
  Balance on fitball/Balance on fitball+ball kick.
  Hypopressive exercises.

Set 3
 Objective: work on cross muscle chains (essential for shooting, playing tennis, golf, and similar).
 Examples:
  Repetitions of the movement to be worked, varying speed and power.
  Proprioception exercises on an unstable surface.
  We start our march at a slow pace.

In a second phase of rehabilitation, we incorporate the trunk garment, the vest, as in the second arrangement of FIG. 10B, to the same exercises (Sets 1, 2 and 3 above) and the trouser garment with the ballast previously used, as in the first arrangement of FIG. 10A. This will allow us, in addition to creating more instability at the level of the knee, forcing us to work even more the stabilizing musculature of the same, to perform a work of the trunk (CORE) very important in the realization of any type of movement of the body (whether of the upper or lower extremity). We will do this by placing the ballast in different positions, according to the desired work.

The exercises to perform would be:

Set 4
 We will start by combining:
  First arrangement (FIG. 10A) and second (FIG. 10B): Exercise set 1.
  First arrangement (FIG. 10A) and third (FIG. 10C1): Exercise set 2 with FIG. 10A and FIG.
  First arrangement (FIG. 10A) and fifth (FIG. 10D): Exercise set 3.
  First arrangement (FIG. 10A) and fourth (FIG. 10C2): Walking.
 Next, to continue evolving, we will continue to increase the combinations and maintain the exercises:
  First arrangement (FIG. 10A), second (FIG. 10B) and third (FIG. 10C1): Exercise sets 1 and 2
  First arrangement (FIG. 10A), third (FIG. 10C1) and fifth (FIG. 10D): Exercise sets 2 and 3
  First arrangement (FIG. 10A) and fourth (FIG. 10C2): Walking and slow march.
  First arrangement (FIG. 10A) and fifth (FIG. 10D): Walking and slow march.

The progression continues by increasing the ballasts and combinations, along with the increase of fluid in the reservoirs (at the discretion of the physiotherapist according to objectives):

First arrangement (FIG. 10A), second (FIG. 10B), fourth (FIG. 10C2), and fifth (FIG. 10D): exercise sets 1, 2, 3.

We finalize with a march with
 First arrangement (FIG. 10A), and third (FIG. 10C1).
 First arrangement (FIG. 10A), and fourth (FIG. 10C2).

The reservoirs are filled from less to more liquid depending on the intensity that the patient can withstand and the objective sought by the physical therapist. Likewise, a denser liquid payload can be used in exercises with less relevant dynamics, for example, planks, bridge, and so on. In these cases, the slower displacement of the interior of the reservoirs makes the work more durable and intense, as it becomes necessary to constantly work to readjust the position to the new situation caused by the constant change of forces resulting from the advance of the liquid through the reservoir.

It should also be noted that this is an example of work for the "average" patient, but that if necessary the intensity can be further increased by adding ballasts on the sides or on the back of the vest, which increases the payload and instability when performing the exercise.

Therefore, the different aspects of the invention described allow configuring, in a flexible and simple manner, different garment configurations that can work a particular area of the body while carrying out another activity. If the other activity is a sporting one, the positive effect of the physical activity or exercise is reinforced, helping to strengthen the musculature of that area of the body, either preventively, or to achieve a desired body shape. On the other hand, the arrangement of ballasts can be adjusted to a specific pathology that needs to be improved and thus treat a particular ailment.

Experimental Results

An example garment, in this case an upper body vest, was used to test the degree to which the body muscles exercise more as a user performs certain activities wearing the vest. The core muscles (rectus abdominis, also known as superior and inferior abdominal muscles) were tested, by connecting them to electrodes, and measuring the muscle activation signal strength in different phases. The core muscle activity was recorded using a surface electromyography EMG system, the Biometrics DataLOG MWX8, using SX230FW EMG sensors. The first phase is the running position, where the user jogs lightly, however wearing no vest. The second phase is the same as the first phase, however the user wears a vest comprising 3 kg of solid ballasts. Finally, the third phase is the same as the second phase, however the users wearing a vest comprising 3 kg of liquid ballasts. In particular, the aim was to determine whether running with a liquid-weighted vest involves a greater effort for the core muscles versus running without load or running with a solid-weighted vest. TABLE I shows the results of the experimentation.

TABLE I

|  |  | Solid Ballast | | Liquid Ballast | |
| --- | --- | --- | --- | --- | --- |
| Core Muscle EMG | Running μV | μV | % difference wrt running | μV | % difference wrt running |
| Superior Left | 3.54 | 3.60 | +1.69 | 10.72 | +202.82 |
| Right | 3.72 | 3.63 | −2.41 | 11.48 | +210.27 |
| Inferior Left | 3.61 | 5.44 | +50.69 | 5.77 | +59.83 |
| Right | 3.78 | 4.04 | +6.87 | 5.91 | +56.34 |

As can be seen, when running with a solid-weighted vest as opposed to running without a vest, the core muscle activity is increased mainly for the inferior muscles. However, the effect is significantly higher when the vest is liquid-weighted, with an increase in muscle activity in both superior (with an average increase of 206.55%) as well as inferior (with an average increase of 58.09%) core muscles. It can also be observed how the greatest impact is on the upper abdominals, possibly because the vest design elevates the center of mass of the user's body, in view of the design used. Nevertheless, further analysis by an expert would be required to determine whether the difference might also be caused due to a past lesion, or structural imbalance, which could be remedied using the garment of the invention.

It is therefore concluded that the technical effect of increased muscle activity as previously described does occur, wherein running with a weighted vest requires the core muscles to work harder. It is also concluded that the required effort is higher for a liquid weighted vest over a solid-weighted one for the upper body garment configuration and exercise routines selected for this experiment.

What has been described comprises one or more embodiments by way of example. It is of course not possible to describe every conceivable combination, or permutation, of the components and/or methodologies for the purpose of describing the aforementioned embodiments. Instead, after a straightforward and objective reading of this disclosure, the skilled artisan will realize that many other combinations and permutations of various embodiments are possible within the described inventive concept. Accordingly, it is intended to embrace all such alterations, modifications and variations that fall within the scope of the appended claims.

In the following, certain additional aspects or examples are described: Garment configured to be worn by a user, the garment comprising at least one reservoir filled with viscous material that generates forces acting on at least one muscle of the user when moving.

The garment, wherein the forces act on the stabilizing musculature, CORE, of unconscious activation. The garment, wherein the forces additionally act by strengthening the active muscles of conscious activation. The garment, wherein the density or viscosity of the viscous material is configurable. The garment, wherein the mass of the viscous material is configurable. The garment, wherein the viscous material is a gel, or any liquid, such as water. The garment, wherein the at least one reservoir is purposefully directionally arranged to generate forces in at least one preselected direction. The garment, wherein the density or viscosity or mass or filler level of the viscous material, or any combination thereof, are configured based on the directionality selected for a given muscle or muscle group. The garment, wherein the at least one reservoir is completely filled with the viscous material. The garment, wherein the at least one reservoir is partially filled with the viscous material. The garment, wherein the at least one reservoir comprises elastic walls. The garment, wherein the at least one reservoir comprises filler means for filling with viscous material. The garment, wherein the at least one reservoir comprises filler means for additionally filling with air. The garment, wherein the at least one reservoir is watertight, is available in different sizes and shapes, and has a predetermined distribution of viscous material and air. The garment, configured to carry, removably or permanently, the at least one reservoir. The garment, wherein the at least one reservoir is configured with a substantially elongated shape ensuring actuation of the viscous filler forces along the longitudinal axis of the reservoir as the user moves. The garment, wherein the longitudinal axis of the at least one reservoir is arranged parallel to the main axis of the muscle tissues on which it acts. The garment, wherein the at least one reservoir is configured with a minimum width allowing viscous filler forces to act in multiple directions within the reservoir as the user moves. The garment, wherein the at least one reservoir is configured with a substantially round or elliptical shape. The garment, wherein the at least one reservoir is disposed on the muscle on which it primarily acts and additionally acts on other adjoining muscles. The garment, comprising multiple reservoirs arranged in multiple directions for the simultaneous working of different muscles. The garment, comprising two reservoirs, the first reservoir arranged on the muscle to be worked, and the second reservoir arranged on the same working axis but away from the first reservoir, exerting a lever effect and increasing the effect of the first reservoir. The garment, wherein the at least one reservoir comprises a high density or high viscosity material, permitting the user's body, as it moves, to readjust slower and more steadily. The garment, wherein the at least one reservoir comprises a low density or low viscosity material, allowing for stabilization of the user's body during higher motion activities. The garment, wherein the at least one reservoir comprises a high mass material, allowing for increased work of the conscious musculature of the user's body when moving. The garment, wherein various parameters of the garment, such as density or viscosity or mass of the filler or amount of filler or reservoir directionality or the arrangement of multiple reservoirs, or any combination thereof, are configurable so that the actuation of the generated forces can be focused on a primary objective. The garment, wherein the primary objective is to act on particular muscles, or on a muscle area in general, or a combination thereof. The garment, wherein the primary objective is to configure a predetermined distribution of the forces between weight and directionality, or a combination thereof. The garment, wherein the primary objective is to improve urinary incontinence, and/or prevent uterine or bladder prolapse and promote postural control, and/or improve respiratory function and/or increase abdominal muscle tone after childbirth, and/or improve posture, increase muscle performance and strength, and/or create muscle and joint receptors, and/or improve proximal stability for greater distal efficiency, and/or stabilize the hip, and/or restore quick grip after a wrist peripheral nerve section, and/or improve proprioception of the wrist complex and increase articular range after wrist carpal tunnel surgery, and/or improve ligamentous proprioception of the ankle after sprain or fracture, and/or regain muscle strength and restore the proprioceptive system after sprain or ACL surgery of the knee. The garment, wherein the garment is a vest type garment for the trunk, or glove type garment for the hands and fingers, or shoes for ankle and/or foot work, or pants for specific work of the hips, and/or knees, and/or ankles, or long-sleeved blouse for shoulder, and/or elbow, and/or back work, or any combination thereof. The garment, wherein the garment is configured of a breathable material. The garment, wherein the garment is configured of a material suitable for aquatic activities.

Article comprising at least two garments according to any one of the preceding claims.

The invention claimed is:

1. A garment configured to be worn by a user, the garment comprising:
   multiple reservoirs arranged in multiple directions and configured to simultaneously work different muscles of a body of the user;
   wherein each reservoir is configured to be filled with viscous material configured to generate forces acting on at least one muscle of the user when moving;
   wherein each reservoir is configured to be purposefully directionally arranged on at least one muscle to generate forces in at least one preselected direction; and
   wherein a parameter of the garment, such as density or viscosity or mass of a filler or amount of filler or reservoir directionality or an arrangement of multiple reservoirs, or any combination thereof, is configured so that an actuation of the generated forces is a function of weight and directionality.

2. The garment of claim 1, wherein the garment is configured such that the forces act on a core musculature responsible for stabilizing the body of the user.

3. The garment of claim 2, wherein the garment is configured such that the forces additionally act by strengthening one or more muscles responsible for body movement.

4. The garment of claim 3, wherein the garment is configured such that a density or viscosity of the viscous material is configurable.

5. The garment of claim 4, wherein the garment is configured such that a mass of the viscous material is configurable.

6. The garment of claim 4, wherein the garment is configured such that the viscous material is a gel, or any liquid.

7. The garment of claim 4, wherein the garment is configured such that each reservoir is completely filled with the viscous material.

8. The garment of claim 4, wherein the garment is configured such that each reservoir is partially filled with the viscous material.

9. The garment of claim 8, wherein the garment is configured such that each reservoir comprises filler means for additionally filling with air.

10. The garment of claim 9, wherein the garment is configured such that a longitudinal axis of each reservoir is arranged parallel to a main axis of muscle tissues on which it acts.

11. The garment of claim 9, wherein the garment is configured such that each reservoir is configured with a round or elliptical shape with a minimum width allowing viscous filler forces to act in multiple directions within the at least one reservoir as the user moves.

12. The garment of claim 4, wherein the garment is configured such that each reservoir comprises elastic walls.

13. The garment of claim 4, wherein the garment is configured such that each reservoir comprises filler means for filling with viscous material.

14. The garment of claim 4, wherein the garment is configured such that each reservoir is
    watertight, is available in different sizes and shapes, and has a predetermined distribution of viscous material and air.

15. The garment of claim 4, wherein the garment is configured such that each reservoir is configured with a substantially elongated shape ensuring actuation of the viscous filler forces along a longitudinal axis of the at least one reservoir as the user moves.

16. The garment of claim 15, wherein the garment is configured such that each reservoir is disposed on a muscle on which it primarily acts but additionally acts on other adjoining muscles.

17. The garment of claim 4,
    comprising two reservoirs, a first reservoir positioned on a muscle, and a second reservoir positioned on a same working axis but away from the first reservoir, exerting a lever effect and increasing an effect of the first reservoir;
    or wherein each of the first and second reservoir comprises a high density or high viscosity material configured for permitting the body of the user to readjust slower and more steadily as the user moves;
    or wherein each of the first and second reservoir comprises a low density or low viscosity material configured for allowing for stabilization of the body of the user during higher motion activities;
    or wherein each of the first and second reservoir comprises a high mass material configured for allowing for increased work of a musculature, responsible for movement, of the body of the user as the user moves.

18. The garment of claim 4,
    wherein the garment is configured to act on particular muscles, or on a muscle area in general, or a combination thereof;
    or wherein the garment is configured to configure a predetermined distribution of the forces between weight and directionality;
    or wherein the garment is configured to improve urinary incontinence, and/or prevent uterine or bladder prolapse and promote postural control, and/or improve respiratory function and/or increase abdominal muscle tone after childbirth, and/or improve posture, increase muscle performance and strength, and/or create muscle and joint receptors, and/or improve proximal stability for greater distal efficiency, and/or stabilize a hip, and/or restore quick grip after a wrist peripheral nerve section, and/or improve proprioception of a wrist complex and increase articular range after wrist carpal tunnel surgery, and/or improve ligamentous proprioception of an ankle after sprain or fracture, and/or regain muscle strength and restore a proprioceptive system after sprain or ACL surgery of a knee.

19. The garment of claim 4,
    wherein the garment comprises a vest type garment suitable for a trunk and/or back;
    or wherein the garment is configured of a breathable material;
    or wherein the garment is configured of a material suitable for aquatic activities.

20. An article comprising at least two garments according to claim 1.

* * * * *